United States Patent
Tajiri et al.

(10) Patent No.: US 10,603,285 B2
(45) Date of Patent: Mar. 31, 2020

(54) SOLID PREPARATION INCLUDING COLORANT

(71) Applicant: DAIICHI SANKYO COMPANY, LIMITED, Tokyo (JP)

(72) Inventors: Shinichiro Tajiri, Kanagawa (JP); Shinji Yoshinaga, Kanagawa (JP); Yurika Ozaki, Kanagawa (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/559,700

(22) PCT Filed: Mar. 17, 2016

(86) PCT No.: PCT/JP2016/058608
§ 371 (c)(1),
(2) Date: Sep. 19, 2017

(87) PCT Pub. No.: WO2016/148264
PCT Pub. Date: Sep. 22, 2016

(65) Prior Publication Data
US 2018/0243223 A1 Aug. 30, 2018

(30) Foreign Application Priority Data
Mar. 19, 2015 (JP) .................. 2015-055769

(51) Int. Cl.
| | | |
|---|---|---|
| *A61K 47/02* | (2006.01) | |
| *A61K 9/28* | (2006.01) | |
| *A61K 31/195* | (2006.01) | |
| *A61K 47/22* | (2006.01) | |
| *A61K 47/12* | (2006.01) | |
| *A61K 47/36* | (2006.01) | |
| *A61K 47/10* | (2017.01) | |
| *A61K 47/38* | (2006.01) | |
| *A61K 47/26* | (2006.01) | |
| *A61K 47/20* | (2006.01) | |
| *A61K 47/14* | (2017.01) | |
| *A61K 9/20* | (2006.01) | |

(52) U.S. Cl.
CPC .......... *A61K 9/2813* (2013.01); *A61K 9/2013* (2013.01); *A61K 9/2018* (2013.01); *A61K 9/2054* (2013.01); *A61K 9/28* (2013.01); *A61K 31/195* (2013.01); *A61K 47/02* (2013.01); *A61K 47/10* (2013.01); *A61K 47/12* (2013.01); *A61K 47/14* (2013.01); *A61K 47/20* (2013.01); *A61K 47/22* (2013.01); *A61K 47/26* (2013.01); *A61K 47/36* (2013.01); *A61K 47/38* (2013.01)

(58) Field of Classification Search
CPC ........ A61K 47/02; A61K 47/12; A61K 47/38; A61K 9/2813; A61K 9/28; A61K 31/195
See application file for complete search history.

(56) References Cited

U.S. PATENT DOCUMENTS

| | | | |
|---|---|---|---|
| 5,032,390 | A | 7/1991 | Iwaya et al. |
| 6,054,482 | A | 4/2000 | Augart et al. |
| 7,351,429 | B1 | 4/2008 | Ohyama et al. |
| 7,794,748 | B2 | 9/2010 | Sugihara et al. |
| 7,947,738 | B2 | 5/2011 | Shimada et al. |
| 8,895,141 | B2 | 11/2014 | Satomi et al. |
| 9,675,570 | B2 | 6/2017 | Tajiri et al. |
| 2001/0004637 | A1 | 6/2001 | Hanamura et al. |
| 2005/0026981 | A1 | 2/2005 | Sugihara et al. |
| 2007/0099986 | A1 | 5/2007 | Ishichi et al. |
| 2009/0041843 | A1 | 2/2009 | Kozaki et al. |

(Continued)

FOREIGN PATENT DOCUMENTS

| | | |
|---|---|---|
| CN | 100379416 C | 4/2008 |
| CN | 101878193 A1 | 11/2010 |

(Continued)

OTHER PUBLICATIONS

Ferin, et al; title: Biological Effects and Toxicity Assessment of Titanium Dioxides: Anatase and Rutile; pp. 69-72, Published online: Jun. 4, 2010). (Year: 2010).*
Cutrignelli et al., "Comparative effects of some hydrophilic excipients on the rate of gabapentin and baclofen lactamization in lyophilized formulations," *International Journal of Pharmaceutics*, (2007), 332:98-106.
Hashida, "The Design and Evaluation of Oral Medications," Published Feb. 10, 1995, by Yakugyo Jiho Co., Tokyo, Japan, pp. 50-51.
Tsuda et al., "Pharmaceutical Engineering, Course X, Fundamentals of Pharmaceutical Development," Published Mar. 1, 1971, by Chijin Shoka Co., Ltd., Tokyo, Japan, pp. 161-162, 167, 170-171, and 179.
(Continued)

*Primary Examiner* — Yanzhi Zhang
(74) *Attorney, Agent, or Firm* — Dorsey & Whitney LLP

(57) ABSTRACT

An object of the present invention is to provide [(1R,5S, 6S)-6-(aminomethyl)-3-ethylbicyclo[3.2.0]hept-3-en-6-yl] acetic acid monobenzenesulfonate as a stabilized pharmaceutical solid preparation, and also to provide a method for preparing the stabilized pharmaceutical solid preparation. The object can be attained by a pharmaceutical solid preparation comprising [(1R,5S,6S)-6-(aminomethyl)-3-ethylbicyclo[3.2.0]hept-3-en-6-yl]acetic acid monobenzenesulfonate which is compound represented by the following formula (I) in combination with (i) one or two or more components selected from the group consisting of D-mannitol, lactose, corn starch, and crystalline cellulose, (ii) carmellose calcium, and (iii) colorants.

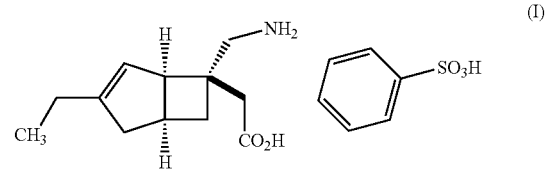

(I)

17 Claims, No Drawings

(56) References Cited

U.S. PATENT DOCUMENTS

| | | | |
|---|---|---|---|
| 2010/0062063 A1* | 3/2010 | Umejima | A61K 9/0056 424/474 |
| 2010/0249229 A1 | 9/2010 | Shimada et al. | |
| 2011/0135927 A1 | 6/2011 | Satomi et al. | |
| 2011/0305758 A1 | 12/2011 | Matono et al. | |
| 2012/0071685 A1 | 3/2012 | Kitagawa et al. | |
| 2012/0156261 A1 | 6/2012 | Fujiwara et al. | |
| 2012/0219637 A1 | 8/2012 | Aniket et al. | |
| 2012/0294947 A1* | 11/2012 | Kuninobu | A61K 9/2077 424/497 |
| 2013/0243859 A1 | 9/2013 | Mima et al. | |
| 2013/0309313 A1 | 11/2013 | Gareau et al. | |
| 2013/0345444 A1 | 12/2013 | Yamano et al. | |
| 2014/0024699 A1 | 1/2014 | Kaelin, Jr. et al. | |
| 2014/0030209 A1 | 1/2014 | Furuta et al. | |
| 2015/0079166 A1* | 3/2015 | Tajiri | A61K 47/10 424/464 |

FOREIGN PATENT DOCUMENTS

| | | |
|---|---|---|
| CN | 104334169 A | 2/2015 |
| EP | 1 205 190 A1 | 5/2002 |
| EP | 1245232 A1 | 10/2002 |
| EP | 2826477 A1 | 1/2015 |
| EP | 3 272 346 A1 | 1/2018 |
| JP | 11-189547 A | 7/1999 |
| JP | 2001-064177 A1 | 3/2001 |
| JP | 2003-104887 A | 4/2003 |
| JP | 2005-263790 A | 9/2005 |
| JP | 2007-131542 A | 5/2007 |
| JP | 2009-275041 A | 11/2009 |
| JP | 4479974 B2 | 6/2010 |
| JP | 2010-241796 A | 10/2010 |
| JP | 2013-35797 A | 2/2013 |
| WO | 01/12193 A1 | 2/2001 |
| WO | 2001/034147 A1 | 5/2001 |
| WO | 2006/056874 A1 | 6/2006 |
| WO | 2007/052592 A1 | 5/2007 |
| WO | 2010/021300 A1 | 2/2010 |
| WO | 2010/087462 A1 | 8/2010 |
| WO | 2013/021660 A1 | 2/2013 |
| WO | 2014/163132 A1 | 10/2014 |

OTHER PUBLICATIONS

Yakuji Nippo Limited, Iyakuhin Tenkabutsu Jiten 2007 (English translation is "Pharmaceutical Excipients Dictionary," 2007), International Pharmaceutical Excipients Council Japan, with English translation, 50 pages.

English Translation of International Search Report dated Jun. 7, 2016, for PCT Application No. PCT/JP2016/058608, 3 pages.

English Translation of Written Opinion dated Jun. 7, 2016, for PCT Application No. PCT/JP2016/058608, 7 pages.

English Translation of International Search Report dated Jun. 7, 2016, for PCT Application No. PCT/JP2016/058607, 3 pages.

English Translation of Written Opinion dated Jun. 7, 2016, for PCT Application No. PCT/JP2016/058607, 6 pages.

English translation of International Search Report dated Apr. 28, 2014, in PCT Application No. PCT/JP2014/059812, 2 pages.

Supplementary Search Report dated Aug. 12, 2015, in European Application No. 14779687.4, 4 pages.

U.S. Appl. No. 15/559,573, filed Mar. 17, 2016, entitled "Solid Preparation Including Antioxidant," 28 pages.

Ferin et al., "Biological Effects and Toxicity Assessment of Titanium Dioxides: Anatase and Rutile," *Am. Ind. Hyg. Assoc. J.*, (1985), 46(2):69-72.

Chen-Feng et al., "Study of Aromatic Nano-$TiO_2$ Modified Acrylic-Polyurethane Composites," *Chemical Materials for Construction*, (2007), 23(2):30-32.

Jing, "Application Directory of Pharmaceutical Excipients," *China Medical Science Press*, Aug. 31, 2011, pp. 187-189.

Zongmao, "Production and Application of a Pharmaceutical Excipient-Thin Film Coating," *China Medical Science Press*, May 31, 2014, pp. 53-61.

\* cited by examiner

SOLID PREPARATION INCLUDING COLORANT

This application is a national stage application under 35 U.S.C. § 371 of International Application No. PCT/JP2016/058608, filed Mar. 17, 2016, entitled "SOLID PREPARATION CONTAINING COLORANT," which claims priority to Japanese Patent Application No. 2015-055769, filed Mar. 19, 2015.

TECHNICAL FIELD

The present invention relates to pharmaceutical solid preparations of [(1R,5S,6S)-6-(aminomethyl)-3-ethylbicyclo[3.2.0]hept-3-en-6-yl]acetic acid monobenzenesulfonate (hereinafter, also referred to as "compound (I)") stabilized by containing colorants, and methods for preparing the stabilized pharmaceutical solid preparations.

The present invention also relates to tablets of compound (I) stabilized by containing colorants, and methods for producing the stabilized tablets.

BACKGROUND ART

Compound (I) represented by the following structural formula:

[Formula 1]

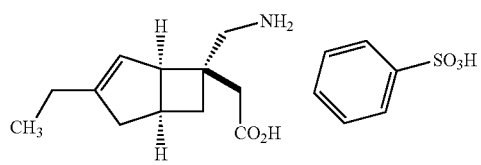

is disclosed in US 2010/249229. This compound (I) has excellent activity as an $\alpha_2\delta$ ligand and as such, is expected to have excellent therapeutic and/or preventive effects on disorders such as pain and central nervous system involvement. Also, pharmaceutical compositions containing compound (I) are disclosed in EP2826477.

CITATION LIST

Patent Literature

Patent Literature 1: US 2010/249229
Patent Literature 2: EP2826477

SUMMARY OF INVENTION

Technical Problem

The present inventors have continuously conducted diligent studies in order to develop pharmaceutical solid preparations of compound (I) stabilized by containing colorants, and methods for preparing the stabilized pharmaceutical solid preparations. Consequently, the present inventors have solved problems associated therewith and completed the present invention.

Solution to Problem

Specifically, the present invention is based on the finding that, as described below, compound (I) represented by the following structural formula:

[Formula 2]

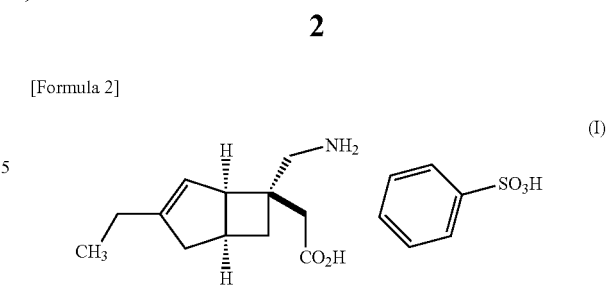

is stabilized by allowing colorants to be present together. Thus, the present invention provides pharmaceutical solid preparations containing this compound (I) and the colorants, and methods for preparing the stabilized pharmaceutical solid preparations.

Preferred aspects of the present invention are as shown below.

[1] A pharmaceutical solid preparation comprising [(1R,5S,6S)-6-(aminomethyl)-3-ethylbicyclo[3.2.0]hept-3-en-6-yl]acetic acid monobenzenesulfonate which is a compound represented by the following formula (I):

[Formula 3]

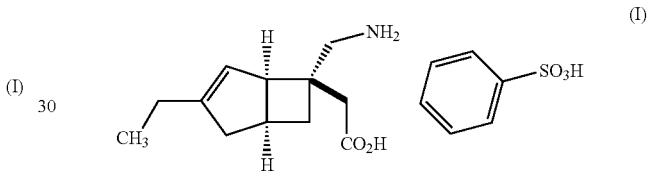

in combination with
(i) one or two or more components selected from the group consisting of D-mannitol, lactose, corn starch, and crystalline cellulose,
(ii) carmellose calcium, and
(iii) titanium oxide as a colorant and one or two or more additional colorants.

[2] The pharmaceutical solid preparation according to [1], wherein the component (i) is D-mannitol.

[3] The pharmaceutical solid preparation according to [2], wherein the D-mannitol is D-mannitol having an average particle size smaller than 150 μm.

[4] The pharmaceutical solid preparation according to [2], wherein the D-mannitol is D-mannitol having an average particle size of 100 μm or smaller.

[5] The pharmaceutical solid preparation according to any one selected from [1] to [4], wherein
the colorants (iii) are titanium oxide and
one or two or more additional colorants selected from the group consisting of red iron sesquioxide, yellow iron sesquioxide, black iron oxide, Blue No. 1, Blue No. 2, Red No. 3, Yellow No. 4, and Yellow No. 5.

[6] The pharmaceutical solid preparation according to any one selected from [1] to [4], wherein the colorants (iii) are titanium oxide, red iron sesquioxide, and yellow iron sesquioxide.

[7] The pharmaceutical solid preparation according to [6], wherein the colorants (iii) are titanium oxide, red iron sesquioxide, and yellow iron sesquioxide, wherein the contents thereof are 0.05 to 0.8% by weight of titanium oxide, 0.003 to 0.01% by weight of red iron sesquioxide, and 0.006 to 0.02% by weight of yellow iron sesquioxide.

[8] The pharmaceutical solid preparation according to any one selected from [5] to [7], wherein the titanium oxide is rutile type titanium oxide.

[9] The pharmaceutical solid preparation according to any one selected from [1] to [8], wherein the content of the carmellose calcium (ii) is 2 to 20% by weight with respect to the total weight.

[10] The pharmaceutical solid preparation according to any one selected from [1] to [8], wherein the content of the carmellose calcium (ii) is 5 to 15% by weight with respect to the total weight.

[11] The pharmaceutical solid preparation according to any one selected from [1] to [10], further comprising magnesium stearate or sodium stearyl fumarate.

[12] The pharmaceutical solid preparation according to any one selected from [1] to [10], further comprising magnesium stearate.

[13] The pharmaceutical solid preparation according to [12], wherein the content of the magnesium stearate is 0.5 to 5% by weight with respect to the total weight.

[14] The pharmaceutical solid preparation according to [12], wherein the content of the magnesium stearate is 1 to 3% by weight with respect to the total weight.

[15] The pharmaceutical solid preparation according to any one selected from [1] to [14], wherein the pharmaceutical solid preparation is a tablet coated with a coating agent, wherein when the colorants (iii) are mixed with the coating agent for use, the amount of the colorants used is 0.05% by weight or higher and 2.0% by weight or lower with respect to the total weight of the uncoated tablet.

[16] The pharmaceutical solid preparation according to any one selected from [1] to [14], wherein the pharmaceutical solid preparation is a tablet coated with a coating agent, wherein when the colorants (iii) are mixed with the coating agent for use, the amount of the colorants used is 0.1% by weight or higher and 1.0% by weight or lower with respect to the total weight of the uncoated tablet.

[17] The pharmaceutical solid preparation according to any one selected from [1] to [16], wherein the content of the compound represented by the formula (I) (in terms of its free form) is 0.5 to 25% by weight with respect to the total weight.

[18] The pharmaceutical solid preparation according to any one selected from [1] to [16], wherein the content of the compound represented by the formula (I) (in terms of its free form) is 0.5 to 5% by weight with respect to the total weight.

[19] A method for stabilizing a pharmaceutical solid preparation in the case of producing the pharmaceutical solid preparation using [(1R,5S,6S)-6-(aminomethyl)-3-ethylbicyclo[3.2.0]hept-3-en-6-yl]acetic acid monobenzenesulfonate which is a compound represented by the following formula (I):

[Formula 4]

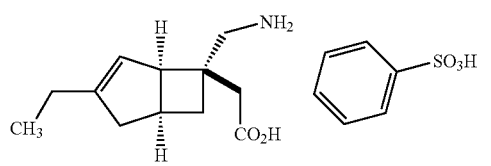

(I)

in combination with
(i) one or two or more components selected from the group consisting of D-mannitol, lactose, corn starch, and crystalline cellulose,
(ii) carmellose calcium, and
(iii) titanium oxide as a colorant and one or two or more additional colorants, the method comprising stabilizing the produced pharmaceutical solid preparation using the colorants.

[20] A method for stabilizing a produced pharmaceutical solid preparation, comprising allowing a coating agent for a coated tablet according to any one of [15] and [16] to contain the colorants (iii) and preparing the produced pharmaceutical solid preparation into the coated tablet.

Advantageous Effects of Invention

The present invention has overcome various difficulties in obtaining a stabilized pharmaceutical solid preparation of compound (I). A feature of the present invention is that the stabilized pharmaceutical solid preparation can be obtained at last by containing colorants, particularly by allowing a coating agent to contain colorants, followed by coating.

The present invention has enabled the preparation of a stabilized pharmaceutical solid preparation of compound (I) and further enabled the production of a stabilized pharmaceutical solid preparation, particularly, in the form of coated tablets, of compound (I).

DESCRIPTION OF EMBODIMENTS (Components and their Preferred Contents)
The compound (I) used as an active ingredient in the present invention has individual particle sizes of preferably 60 μm (more preferably 40 μm) or smaller in terms of d50 particle size.

The content of compound (I) (in terms of its free form) used in the present invention is preferably 0.5 to 40% by weight, more preferably 0.5 to 25% by weight, particularly preferably 0.5 to 10% by weight (more particularly preferably 0.5 to 5% by weight), with respect to the total weight.

The content of excipient (preferably D-mannitol) used in the present invention is preferably 50 to 90% by weight, more preferably 60 to 90% by weight with respect to the total weight.

The average particle size of the D-mannitol used in the present invention is desirably smaller than 150 μm, preferably 120 μm or smaller, more preferably 100 μm or smaller, particularly preferably 80 μm or smaller.

The content of disintegrant (preferably carmellose calcium, etc.) used in the present invention is preferably 2 to 20% by weight, more preferably 5 to 15% by weight, with respect to the total weight.

The content of binder (preferably hypromellose, etc.) used in the present invention is preferably 5 to 20% by weight with respect to the total weight.

The content of lubricant (preferably magnesium stearate, sodium stearyl fumarate, etc., particularly preferably magnesium stearate) used in the present invention is preferably 0.5 to 5% by weight, more preferably 1 to 3% by weight, with respect to the total weight.

The coating agent used in the present invention is a coating agent whose use is generally acceptable in the medical field and is a coating agent described in general references, etc. The coating agent is described in, for example, Japanese Pharmaceutical Excipients 2007 (edited by International Pharmaceutical Excipients Council Japan, published by Yakuji Nippo Ltd.). Preferably, hypromellose, polyethylene glycol, polyvinyl alcohol (PVA), ethylcellulose, carboxymethylcellulose sodium, maltodextrin, dextrose, stearic acid, triethyl citrate, glyceryl monostearate, xanthan gum, triacetin, titanium oxide, talc, macrogol, lactose, hydroxypropylcellulose, light anhydrous silicic acid, soybean lecithin, colorants, etc. are appropriately mixed and used.

When a commercially available premix product is used as the coating agent, examples thereof include OPADRY OY-S9607, OPADRY 01A430004, OPADRY 01A440001, OPADRY 01A430000, OPADRY 01A440004, OPADRY 01A480009, OPADRY 200, OPADRY amb, OPADRY fx, and OPADRY II manufactured by Colorcon Japan LLC. OPADRY 01A430004, OPADRY 01A440001, OPADRY 01A430000, OPADRY 01A440004, OPADRY 01A480009, or the like is preferred.

The colorants used in the present invention are colorants whose use is generally acceptable in the medical field. Examples thereof include red iron sesquioxide, yellow iron sesquioxide, black iron oxide, titanium oxide, Blue No. 1 (brilliant blue FCF), Blue No. 2 (indigo carmine), Red No. 3 (erythrosine), Yellow No. 4 (tartrazine), and Yellow No. 5 (sunset yellow FCF).

Red iron sesquioxide, yellow iron sesquioxide, black iron oxide, and titanium oxide are preferred, and red iron sesquioxide, yellow iron sesquioxide, and titanium oxide are particularly preferred.

The crystal form of the titanium oxide used in the present invention is anatase type or rutile type whose use is industrially generally acceptable. Rutile type is particularly preferred.

In a tablet, the total content of the coating agent and the colorants used in the present invention is preferably 3% by weight or higher and 10% by weight or lower with respect to the total weight of the uncoated tablet.

The weight of the colorants with respect to the total weight of the uncoated tablet is preferably 0.05% by weight or higher, more preferably 0.1% by weight or higher, and is preferably 2.0% by weight or lower, more preferably 1.0% by weight or lower.

In the tablet according to the present invention, the preferred content of each component with respect to the total weight of its uncoated tablet is as follows:

Compound (I) (in terms of its free form): 0.5 to 25% by weight

Excipient (preferably D-mannitol): 50 to 90% by weight (average particle size: smaller than 150 µm)

Disintegrant (carmellose calcium): 2 to 20% by weight

Lubricant (preferably magnesium stearate): 0.5 to 5% by weight

The content of each component is more preferably as follows:

Compound (I) (in terms of its free form): 0.5 to 10% by weight

Excipient (D-mannitol): 60 to 90% by weight (average particle size: 100 µm or smaller)

Disintegrant (carmellose calcium): 5 to 15% by weight

Lubricant (magnesium stearate): 1 to 3% by weight

In the coated tablet according to the present invention, the preferred content of each component of the coating agent with respect to the total weight of its uncoated tablet is as follows:

For the coating agent, hypromellose, talc, and the colorants are preferably mixed and used in an amount of 3 to 10% by weight.

The amount of the colorants used is preferably 0.05 to 2.0% by weight. For example, red iron sesquioxide, yellow iron sesquioxide, and titanium oxide are used in an amount of 0.7% by weight in total including 0.005% by weight of red iron sesquioxide, 0.01% by weight of yellow iron sesquioxide, and 0.685% by weight of titanium oxide. For example, red iron sesquioxide, yellow iron sesquioxide, and titanium oxide are used in an amount in total of 0.7% by weight including 0.01% by weight of red iron sesquioxide, 0.02% by weight of yellow iron sesquioxide, and 0.67% by weight of titanium oxide. Preferably, uncoated tablets are prepared into coated tablets using the coating agent containing these colorants.

(Method for Producing Solid Preparation)

The solid preparation of the present invention is obtained in the form of tablets, coated tablets, or the like by sequentially subjecting a powder of compound (I) serving as an active ingredient to, for example:

(1) a step of adding stabilizers such as an excipient and a disintegrant, and further adding auxiliaries necessary for formulation (a lubricant, etc.);

(2) a tableting step of compressing the resulting granular powder using a tableting machine; and (3) an optional coating step of coating the surface of the resulting tablets.

Examples of the method for producing the solid preparation include:

(1) a direct compression method which involves mixing the active ingredient with additives and directly compression-molding the mixture using a tableting machine;

(2) a semi-direct compression method which involves granulating additives, mixing the granules with the active ingredient, and compression-molding the mixture;

(3) a dry granule compression method which involves granulating the active ingredient and additives by a dry process, then adding a lubricant, etc. to the granules, and compression-molding the mixture; and (4) a wet granule compression method which involves granulating the active ingredient and additives by a wet process, then adding a lubricant, etc. to the granules, and compression-molding the mixture.

An approach such as fluidized-bed granulation, high-speed mixer granulation, or melt granulation can be used as a granulation method.

In the present invention, a method which involves preparing a tablet by directly compressing a mixed powder of the active ingredient without granulating a powder of the active ingredient is preferred.

For example, the method for producing a tablet according to the present invention is performed as described below.

The compound (I) serving as an active ingredient is pulverized. The particle size of the resulting powder is adjusted. Then, an excipient and/or a disintegrant are added to the powder, followed by mixing. Then, the mixture is sifted through a particle size selector. Then, a lubricant is added thereto, followed by further mixing. Then, the mixture is compressed using a tableting machine to obtain uncoated tablets.

The obtained uncoated tablets are prepared into coated tablets using a coating apparatus.

Hereinafter, the present invention will be described in more detail with reference to the Examples. However, it should be understood that the Examples below are provided merely for describing the present invention and are not intended to limit the present invention.

EXAMPLES (Example 1) Stability Test on Colorant (1) Preparation of Coated Tablet of Example 1

Mixing and Sifting

Compound (I), D-mannitol, and carmellose calcium were weighed at mixing ratios shown in Table 1 described below, and mixed for 2 minutes at the number of revolutions of 31 rpm using a V-shaped mixer (60 L).

The mixture was sifted at 600 rpm using COMIL (QC-194S, Φ1.143, QUADRO) to prepare a sifted powder.

Subsequently, magnesium stearate was weighed at a mixing ratio shown in Table 1 and added to the sifted powder, followed by mixing for 6 minutes at the number of revolutions of 31 rpm using a V-shaped mixer (60 L).

Compression

The mixture was molded at a compressive pressure of approximately 12 kN using a tableting machine (Virgo, Kikusui Seisakusho Ltd.) to obtain uncoated tablets (containing 2.5% of compound (I) in terms of its free form, oblong tablets, 10.6×5.6 mm) each having a tablet mass of 200 mg.

Coating

OPADRY was dispersed (12.5 w/w %) in purified water using a stirrer (Z-2200, Tokyo Rika Kikai Co., Ltd.) and sifted through a 100-mesh sieve to prepare a coating solution.

The uncoated tablets were coated using a coating apparatus (DRC300, Powrex Corp.) at a charge air temperature of 70° C., a charge air volume of 1.0 m$^3$/min, a spray rate of approximately 7 g/min, the number of pan revolutions of 20 rpm, and an exhaust gas temperature of approximately 36° C. (endpoint) to obtain coated tablets.

(2) Preparation of Coated Tablets of Examples 2 to 7 and Comparative Examples 1 and 2

The respective coated tablets of Examples 2 to 7 and Comparative Examples 1 and 2 were prepared by the preparation method of Example 1 using each component and its content shown in Table 1.

TABLE 1

| Component contained | Composition (mg/tablet) | | | | | | | | |
|---|---|---|---|---|---|---|---|---|---|
| | Example 1 | Example 2 | Example 3 | Example 4 | Example 5 | Example 6 | Example 7 | Comparative Example 1 | Comparative Example 2 |
| Compound (I) (mg in terms of free form) | 8.78 (5) | 8.78 (5) | 8.78 (5) | 8.78 (5) | 8.78 (5) | 8.78 (5) | 8.78 (5) | 8.78 (5) | 8.78 (5) |
| D-mannitol (Parteck M100, Merck) | 167.22 | 167.22 | 167.22 | 167.22 | 167.22 | 167.22 | 167.22 | 167.22 | 167.22 |
| Carmellose calcium (E.C.G-505, Gotoku Chemical Co., Ltd.) | 20 | 20 | 20 | 20 | 20 | 20 | 20 | 20 | 20 |
| Magnesium stearate (Parteck LUB, Merck) | 4 | 4 | 4 | 4 | 4 | 4 | 4 | 4 | 4 |
| OPADRY (Colorcon Japan LLC) | 6 | 8 | 10 | 6 | 8 | 10 | 10 | 10 | 10 |
| (Hypromellose) | (4.32) | (5.76) | (7.2) | (4.32) | (5.76) | (7.2) | (7.2) | (7.2) | (7.2) |
| (Titanium oxide: anatase type) | (0.822) | (1.096) | (1.37) | (0.804) | (1.072) | (1.34) | | (1.4) | |
| (Titanium oxide: rutile type) | | | | | | | (1.34) | | (1.4) |
| (Talc) | (0.84) | (1.12) | (1.4) | (0.84) | (1.12) | (1.4) | (1.4) | (1.4) | (1.4) |
| (Red iron sesquioxide) | (0.006) | (0.008) | (0.01) | (0.012) | (0.016) | (0.02) | (0.02) | — | — |
| (Yellow iron sesquioxide) | (0.012) | (0.016) | (0.02) | (0.024) | (0.032) | (0.04) | (0.04) | — | — |
| Total | 206 | 208 | 210 | 206 | 208 | 210 | 210 | 210 | 210 |

TABLE 2

| Component of coating agent | Ratios of coating agent and colorant (% by weight/uncoated tablet) | | | | | | | | |
|---|---|---|---|---|---|---|---|---|---|
| | Example 1 | Example 2 | Example 3 | Example 4 | Example 5 | Example 6 | Example 7 | Comparative Example 1 | Comparative Example 2 |
| Hypromellose | 2.16 | 2.88 | 3.6 | 2.16 | 2.88 | 3.6 | 3.6 | 3.6 | 3.6 |
| Titanium oxide: anatase type | 0.411 | 0.548 | 0.685 | 0.402 | 0.536 | 0.67 | — | 0.7 | — |
| Titanium oxide: rutile type | — | — | — | — | — | — | 0.67 | — | 0.7 |
| Talc | 0.42 | 0.56 | 0.7 | 0.42 | 0.56 | 0.7 | 0.7 | 0.7 | 0.7 |

TABLE 2-continued

| Component of coating agent | Ratios of coating agent and colorant (% by weight/uncoated tablet) | | | | | | | | |
|---|---|---|---|---|---|---|---|---|---|
| | Example 1 | Example 2 | Example 3 | Example 4 | Example 5 | Example 6 | Example 7 | Comparative Example 1 | Comparative Example 2 |
| Red iron sesquioxide | 0.003 | 0.004 | 0.005 | 0.006 | 0.008 | 0.01 | 0.01 | 0 | 0 |
| Yellow iron sesquioxide | 0.006 | 0.008 | 0.01 | 0.012 | 0.016 | 0.02 | 0.02 | 0 | 0 |
| Total | 3 | 4 | 5 | 3 | 4 | 5 | 5 | 5 | 5 |

(3) Evaluation Method and Results

The tablets of Examples 1 to 7 and Comparative Examples 1 and 2 were left under conditions involving 25° C., 65% RH, 25 days (2000 lux/hr), and an open condition. Then, the amount of related substances was measured by HPLC (1290 Infinity, Agilent Technologies, Inc.).
(HPLC Analysis Condition)

TABLE 3

| | |
|---|---|
| Measurement wavelength | 215 nm |
| Column | Sunshell C18 (2.1 mmID × 100 mm, 2.6 μm, manufactured by Chromanik Technologies Inc.) |
| Guard column | SecurityGuard ULTRA C18 (2.1 mmID, manufactured by Phenomenex Inc.) |
| Cleanup column | Ghost Trap DS (7.6 mmID × 30 mm, manufactured by Shimadzu Corp.) |
| Column temperature | 45° C. |
| Mobile phase A | 0.01 mol/L diammonium hydrogen phosphate buffer solution |
| Mobile phase B | Methanol/acetonitrile/0.01 mol/L diammonium hydrogen phosphate buffer solution (pH 6.2) mixed solution (9:3:4) |
| Analysis time | 35 min |
| Injection volume | 3 μL |
| Sample cooler temperature | Constant temperature around 6° C. |

The results are shown in Table 4 (amount of increase from the initial total amount of related substances, %).

The amount of increase from the initial total amount of related substances increased by light was reduced in the coated tablets containing rutile type titanium oxide as a colorant (Comparative Example 2), as compared with the coated tablets containing anatase type titanium oxide (Comparative Example 1).

The amount of increase from the initial total amount of related substances increased by light was shown to be very small (½ to ¼) in the coated tablets containing red iron sesquioxide and yellow iron sesquioxide as colorants in the coating agent (Examples 1 to 7), as compared with the tablets free from these colorants (Comparative Examples 1 and 2). Furthermore, the related substances increased by light were shown not to be generated (equal to or lower than the quantification limit) in the coated tablets containing rutile type titanium oxide (Example 7).

TABLE 4

| Condition | Example 1 | Example 2 | Example 3 | Example 4 | Example 5 | Example 6 | Example 7 | Comparative Example 1 | Comparative Example 2 |
|---|---|---|---|---|---|---|---|---|---|
| 25° C./60% RH/25 days Open condition Light exposed, 1200000 lux (2000 Lux/hr) | 0.19 | 0.13 | 0.11 | 0.12 | 0.09 | 0.08 | <0.05 | 0.39 | 0.30 |
| 25° C./60% RH/25 days Open condition Light shielded, 1200000 lux (2000 Lux/hr) | <0.05 | <0.05 | <0.05 | <0.05 | <0.05 | <0.05 | <0.05 | <0.05 | <0.05 |

Production Examples

Hereinafter, Production Examples of the present invention will be shown. It should be understood that these Production Examples are not intended to limit the present invention.

TABLE 5

| Component contained | Composition (mg/tablet) | | | | | | | |
|---|---|---|---|---|---|---|---|---|
| | Production Example 1 | Production Example 2 | Production Example 3 | Production Example 4 | Production Example 5 | Production Example 6 | Production Example 7 | Production Example 8 |
| Compound (I) (mg in terms of free form) | 8.78 (5) | 8.78 (5) | 8.78 (5) | 8.78 (5) | 8.78 (5) | 8.78 (5) | 8.78 (5) | 8.78 (5) |

TABLE 5-continued

| Component contained | Composition (mg/tablet) | | | | | | | |
|---|---|---|---|---|---|---|---|---|
| | Production Example 1 | Production Example 2 | Production Example 3 | Production Example 4 | Production Example 5 | Production Example 6 | Production Example 7 | Production Example 8 |
| D-mannitol (Parteck M100, Merck) | 161.02 | 161.02 | 161.02 | 161.02 | 154.82 | 154.82 | — | — |
| Carmellose calcium (E.C.G-505, Gotoku Chemical Co., Ltd.) | 20 | 20 | 20 | 20 | 20 | 20 | 20 | 20 |
| Magnesium stearate (Parteck LUB, Merck) | 4 | 4 | 4 | 4 | 4 | 4 | 4 | 4 |
| Citric acid hydrate | 6.2 | 6.2 | — | — | 6.2 | 6.2 | — | — |
| Tocopherol | — | — | 6.2 | 6.2 | 6.2 | 6.2 | — | — |
| β-Cyclodextrin | — | — | — | — | — | — | 167.22 | 167.22 |
| OPADRY (Colorcon Japan LLC) | 10 | 10 | 10 | 10 | 10 | 10 | 10 | 10 |
| (Hypromellose) | (7.2) | (7.2) | (7.2) | (7.2) | (7.2) | (7.2) | (7.2) | (7.2) |
| (Titanium oxide: rutile type) | (1.34) | (1.34) | (1.34) | (1.34) | (1.34) | (1.34) | (1.34) | (1.34) |
| (Talc) | (1.4) | (1.4) | (1.4) | (1.4) | (1.4) | (1.4) | (1.4) | (1.4) |
| (Red iron sesquioxide) | (0.02) | (0.04) | (0.02) | (0.04) | (0.02) | (0.04) | (0.02) | (0.04) |
| (Yellow iron sesquioxide) | (0.04) | (0.02) | (0.04) | (0.02) | (0.04) | (0.02) | (0.04) | (0.02) |
| Total | 210 | 210 | 210 | 210 | 210 | 210 | 210 | 210 |

The invention claimed is:

1. A method of stabilizing a pharmaceutical preparation comprising producing a pharmaceutical preparation comprising [(1R,5S,6S)-6-(aminomethyl)-3-ethylbicyclo[3.2.0] hept-3-en-6-yl]acetic acid monobenzenesulfonate of formula (I):

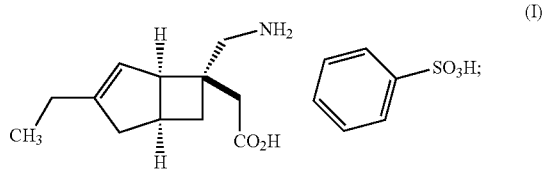

(i) one or two or more components selected from the group consisting of D-mannitol, lactose, corn starch, and crystalline cellulose;
(ii) carmellose calcium; and
(iii) rutile type titanium oxide, red iron sesquioxide, and yellow iron sesquioxide as colorants,
wherein the pharmaceutical preparation is a tablet coated with a coating agent, the colorants are mixed with the coating agent, and the colorants stabilize the pharmaceutical preparation.

2. The method of claim 1, wherein the component (i) is D-mannitol.

3. The method of claim 2, wherein the D-mannitol has an average particle size smaller than 150 μm.

4. The method of claim 2, wherein the D-mannitol has an average particle size of 100 μm or smaller.

5. The method of claim 1, wherein the colorants are titanium oxide present at 0.05 to 0.8% by weight, red iron sesquioxide present at 0.003 to 0.01% by weight, and yellow iron sesquioxide present at 0.006 to 0.02% by weight.

6. The method of claim 1, wherein the carmellose calcium is present at 2 to 20% by weight of the total weight of the preparation.

7. The method of claim 1, wherein the carmellose calcium is present at 5 to 15% by weight of the total weight of the preparation.

8. The method of claim 1, further comprising magnesium stearate or sodium stearyl fumarate.

9. The method of claim 1, further comprising magnesium stearate.

10. The method of claim 9, wherein the magnesium stearate is present at 0.5 to 5% by weight of the total weight of the preparation.

11. The method of claim 9, wherein the magnesium stearate is present at 1 to 3% by weight of the total weight of the preparation.

12. The method of claim 1, wherein the colorants are present at 0.05% to 2.0% by weight of the total weight of the uncoated tablet.

13. The method of claim 1, wherein the colorants are present at 0.1% to 1.0% by weight of the total weight of the uncoated tablet.

14. The method of claim 1, wherein the compound of formula (I) is present at 0.5 to 25% by weight of the total weight of the preparation.

15. The method of claim 1, wherein the compound of formula (I) is present at 0.5 to 5% by weight of the total weight of the preparation.

16. A method of stabilizing a pharmaceutical preparation, comprising:
producing the coated tablet of claim 12 by adding the component (i) to the compound of formula (I) to produce a granular powder, compressing the granular powder to produce a tablet, and coating the surface of the tablet with a coating agent.

17. A method of stabilizing a pharmaceutical preparation, comprising:
producing the coated tablet of claim 13 by adding the component (i) to the compound of formula (I) to produce a granular powder, compressing the granular powder to produce a tablet, and coating the surface of the tablet with a coating agent.

* * * * *